(12) United States Patent
McMillen et al.

(10) Patent No.: US 8,740,910 B2
(45) Date of Patent: Jun. 3, 2014

(54) MODULAR ANTERIOR-POSTERIOR FEMORAL SIZER

(75) Inventors: Troy Allen McMillen, Milford, PA (US); Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1814 days.

(21) Appl. No.: 11/330,512

(22) Filed: Jan. 12, 2006

(65) Prior Publication Data

US 2007/0173851 A1    Jul. 26, 2007

(51) Int. Cl.
*A61B 17/58*      (2006.01)

(52) U.S. Cl.
USPC .............................................. 606/88; 606/87

(58) Field of Classification Search
USPC ............................. 606/87, 88, 86 R, 102, 99; 623/20.14–20.19
See application file for complete search history.

(56) References Cited

U.S. PATENT DOCUMENTS

| | | | |
|---|---|---|---|
| 4,517,969 A | | 5/1985 | Halcomb, III et al. |
| 5,053,037 A | * | 10/1991 | Lackey .............................. 606/79 |
| 5,071,438 A | | 12/1991 | Jones et al. |
| 5,129,907 A | | 7/1992 | Heldreth et al. |
| 5,147,406 A | | 9/1992 | Houston et al. |
| 5,148,920 A | | 9/1992 | Walker |
| 5,181,925 A | | 1/1993 | Houston et al. |
| 5,364,401 A | * | 11/1994 | Ferrante et al. .................. 606/84 |
| 5,405,398 A | | 4/1995 | Buford, III et al. |
| 5,423,827 A | * | 6/1995 | Mumme et al. .................. 606/96 |
| 5,474,559 A | | 12/1995 | Bertin et al. |
| 5,486,178 A | * | 1/1996 | Hodge .............................. 606/82 |
| 5,514,140 A | * | 5/1996 | Lackey .............................. 606/80 |
| 5,540,696 A | | 7/1996 | Booth, Jr. et al. |
| 5,554,158 A | | 9/1996 | Vinciguerra et al. |
| 5,624,444 A | * | 4/1997 | Wixon et al. .................... 606/88 |
| 5,662,656 A | | 9/1997 | White |
| 5,720,752 A | * | 2/1998 | Elliott et al. ...................... 606/88 |
| 5,743,915 A | | 4/1998 | Bertin et al. |
| 5,769,855 A | | 6/1998 | Bertin et al. |
| 5,776,137 A | * | 7/1998 | Katz ................................ 606/88 |
| 5,853,415 A | | 12/1998 | Bertin et al. |
| 5,860,981 A | | 1/1999 | Bertin et al. |
| 5,972,034 A | | 10/1999 | Hofmann et al. |
| 6,013,081 A | | 1/2000 | Burkinshaw et al. |

(Continued)

OTHER PUBLICATIONS

Stryker Howmedica Osteonics, Femoral Preparation, Duracon and Scorpio Total Knee Systems Surgical Protocol, Xcelerate, (2000) pp. 8-9.

(Continued)

*Primary Examiner* — Jan Christopher Merene

(74) *Attorney, Agent, or Firm* — Lerner, David, Littenberg, Krumholz & Mentlik, LLP

(57) ABSTRACT

The invention provides an apparatus and method for sizing a distal portion of a femur during knee arthroplasty. A sizer according to the invention includes a body that can be removably attached to the distal portion of the femur and that is operable to support a module that is removably attachable to the body. The body with attached module is operable for use in measuring the size of the distal portion of the femur. The module can be attached to the body either before or after the body has been attached to the distal portion of the femur and can be detached from the body either before or after the body is detached from the distal portion of the femur.

10 Claims, 10 Drawing Sheets

(56) References Cited

U.S. PATENT DOCUMENTS

| | | | |
|---|---|---|---|
| 6,024,746 | A | 2/2000 | Katz |
| 6,074,424 | A | 6/2000 | Perrone, Jr. et al. |
| 6,106,529 | A * | 8/2000 | Techiera .................. 606/88 |
| 6,290,704 | B1 | 9/2001 | Burkinshaw et al. |
| 6,361,506 | B1 | 3/2002 | Saenger et al. |
| 6,458,135 | B1 | 10/2002 | Harwin et al. |
| 6,468,280 | B1 | 10/2002 | Saenger et al. |
| 7,488,324 | B1 * | 2/2009 | Metzger et al. .......... 606/89 |
| 2002/0029045 | A1 | 3/2002 | Bonutti |
| 2004/0022583 | A1 | 2/2004 | Bussey et al. |
| 2004/0153085 | A1 * | 8/2004 | Farling et al. .......... 606/87 |
| 2004/0220583 | A1 | 11/2004 | Pieczynski, II et al. |
| 2005/0021039 | A1 * | 1/2005 | Cusick et al. .......... 606/88 |
| 2005/0149042 | A1 * | 7/2005 | Metzger .................. 606/88 |
| 2009/0149859 | A1 * | 6/2009 | Metzger et al. .......... 606/89 |

OTHER PUBLICATIONS

Biomet Orthopedics, Inc., Microplasty Instrumentation, Microplasty Minimally Invasive Knee Instruments, (2004) p. 3.

Howmedica, Pfizer Hospital Products Group, Inc., P.C.A. Modular Total Knee System, (1989) pp. 32-33.

Kinemax Plus, Howmedica Surgical Techniques, Kinemax Plus Condylar Knee Kinemax Plus Stabilizer Knee Sugical Technique with the Howmedica Kinemax Plus Knee Instruments, Pfizer HPG, (1992) p. 7.

Howmedica, Inc., Kinemax Plus Total Knee System Operative Technique Highlights, Kinemax Plus Total Knee System, Monogram Total Knee Instruments, (1998) pp. 6-7.

Osteonics Corporation, Passport Posterior Referencing Instrumentaion, The Series 7000 Total Knee System Surgical Protocol, (1997 pp. 9-10).

Stryker Howmedica Osteonics, Duracon Total Knee Systems Surgical Protocol, Duracon CR, Xcelerate Instrumentation, (2003) pp. 8-9.

DePuy Inc., the Concept of Personalization, The AMK Total Knee System Instrumentation Legend II, (1992) pp. 12-13.

DePuy Orthopaedic, Inc., P.F.C. Sigma Rotating Platform Knee System with M.B.T. Tray, (2000) pp. 11-16.

Howmedica, Inc., INTERAX The Total Knee System, (1993) 20 pgs.

Interax, the total knee system, Howmedica International, 1993.

* cited by examiner

MODULAR ANTERIOR-POSTERIOR FEMORAL SIZER

FIELD OF THE INVENTION

The present invention relates to methods and tools used in knee arthroplasty. More particularly, the invention relates to methods and tools used in knee surgery involving the installation of an artificial femoral component.

BACKGROUND OF THE INVENTION

Total knee arthroplasty involves the replacement of portions of the patellar, femur and tibia with artificial components. In particular, a proximal portion of the tibia and a distal portion of the femur are cut away (resected) and replaced with artificial components.

As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner. However, when a tool or instrument is fixated to a bone or other body part the terms "proximal" and "distal" are applied to the tool or instrument as if the tool or instrument were itself a bone or body part.

There are several types of knee prostheses known in the art. One type is sometimes referred to as a "resurfacing type." In these prostheses, the articular surface of the distal femur and proximal tibia are "resurfaced" with respective metal and plastic condylar-type articular bearing components.

The femoral component is typically a metallic alloy construction (e.g. cobalt-chrome alloy or 6A4V titanium alloy) and provides medial and lateral condylar bearing surfaces of multi-radii design of similar shape and geometry as the natural distal femur or femoral-side of the knee joint.

One important aspect of these procedures is the correct resection of the distal femur and proximal tibia. These resections must provide planes which are correctly oriented in order to properly accept the prosthetic components. Among the factors that are considered when assessing resection of the distal femur and proximal tibia are the proximal-distal location of the resection planes, the varus-valgus angle of the planes, and the change in relative orientation of the planes in response to change in flexion-extension angle of the knee.

Moreover, following distal resection the femur is shaped with the aid of a cutting block. To ensure correct shaping of the femur, the cutting block must be correctly positioned and sized. More specifically, the cutting block must be correctly positioned with respect to the anterior-posterior direction and must be correctly rotated about an axis perpendicular to the distal resection plane such that the block's rotation corresponds to the correct Internal/External (I/E) rotation of the femur relative to the tibia. The I/E rotation may be set in a number of ways. One way of setting I/E rotation is by referencing the angle formed between the cutting block's medial-lateral axis as projected onto the distal resection plane and the knee's posterior condylar axis as projected onto the distal resection plane. In a typical case, the angle formed between the cutting block's medial-lateral axis as projected onto the distal resection plane and the knee's posterior condylar axis as projected onto the distal resection plane is set to approximately 3 degrees and matches the angle formed between the epicondylar axis as projected onto the distal resection plane and the posterior condylar axis as projected onto the distal resection plane.

In addition, the cutting block should be correctly positioned with respect to the medial-lateral direction. However, medal-lateral positioning of the block is not critical to the femur shaping procedure and, as such, does not require the same degree of precision as exercised during anterior-posterior positioning of the block and I/E rotation of the block.

A typical cutting block includes two or more fixation pegs, or "pins" that are used for positioning the block on the distal resection plane and securing the block to the plane. In practice, the block to be used is known and thus the positions of the pins within the block are known. Therefore, one can set the block's position in space by setting the pins' position in space. Accordingly, to position the block on the distal plane the appropriate pin positions are determined, pinholes are drilled at the determined positions, the pins in the block are lined up with the pinholes, and the pins are inserted into the pinholes to secure the block to the femur.

In many cases, the appropriate cutting block and the correct pinhole positions are determined using an instrument referred to as an "Anterior-Posterior Sizer" (or "AP Sizer"). The Sizer is designed to determine the appropriate cutting block and correct pinhole positions based on the type and size of femoral component that will be implanted. For example, the implant could be from the line of implants associated with the Stryker® Triathlon® Knee System which includes femoral implants of sizes 1-8. In such context, the AP Sizer will determine the size of Triathlon® implant that is needed and will indicate where the pinholes should be located for a cutting block corresponding to the Triathlon® implant of the determined size.

However, implants from different manufacturers or different lines may differ. Accordingly the cutting blocks and associated hole positions needed for each type of implant may differ, and therefore the AP Sizers required for each type of implant may differ. For this reason, a large number of different AP Sizers is typically required to support a large number of implant-types.

Further, there are many different types of methodologies employed for determining the correct implant size and hole position. For example, implant size and hole position can be determined through use of a "mechanical stylus," a "navigation stylus," a "blade runner," or "drill sizing." The type of sizing used in a procedure is often left to the discretion of the practitioner, with most practitioners having a preference for one method over the others.

For purposes of clarity of presentation, the various types of methodologies employed for determining the correct implant size and hole position will hereinafter be collectively referred to as "sizing methodologies."

Despite the many different sizing methodologies that may be employed, AP Sizers are typically designed for only one methodology. Thus, if a practitioner would like to change methodologies, the practitioner would have to change sizers. For example, a practitioner who prefers blade runner sizing may find that blade runner sizing is inaccurate on a particular patient due to patient specific conditions such as taught muscle tone or localized trauma to the desired referencing zone. In such event, the practitioner may wish to size through navigation rather than blade running. However, to make the change from blade runner sizing to navigation sizing, the practitioner would need to change from a sizer designed for blade runner sizing to a sizer designed for navigation sizing.

In short, prior AP Sizers have been implant-specific and methodology-specific, and therefore large numbers of AP Sizers have been required to support the various implant types and sizing methodologies.

SUMMARY OF THE INVENTION

In view of the desirability of an AP sizer that can efficiently support a number of different implant types and a number of different sizing methodologies, the present invention was conceived.

The invention provides an apparatus and method for sizing a distal portion of a femur during knee arthroplasty. A sizer according to the invention includes a body that can be removably attached to the distal portion of the femur and that is operable to support a module that is removably attachable to the body. The body with attached module is operable for use in measuring the size of the distal portion of the femur. The module can be attached to the body either before or after the body has been attached to the distal portion of the femur and can be detached from the body either before or after the body is detached from the distal portion of the femur.

In this manner, modules specific to various implant types and sizing methodologies can be provided and the sizer can be adapted to support the various types and methodologies by merely interchanging the modules. Further, modules can be changed while the sizer body is in situ, such that alternative types and/or methodologies can be employed during a procedure without the need to detach the sizer body from the femur. Moreover, the readily interchangeable modules facilitate the use of multiple sizing methodologies during a given procedure. The measurements provided according to multiple methodologies can then be used to cross-validate each other.

DESCRIPTION OF THE DRAWINGS

The following detailed description, given by way of example, but not intended to limit the invention solely to the specific embodiments described, may best be understood in conjunction with the accompanying drawings wherein like reference numerals denote like elements and parts, in which.

DETAILED DESCRIPTION OF PREFERRED EMBODIMENTS

FIGS. 1A-1F provide an overview of how a sizer according to one embodiment of the invention can be assembled and attached to a distal portion of a femur. The figures are introductory and a more detailed description of the preferred embodiments is provided in connection with FIGS. 2-9.

Figure 1A:
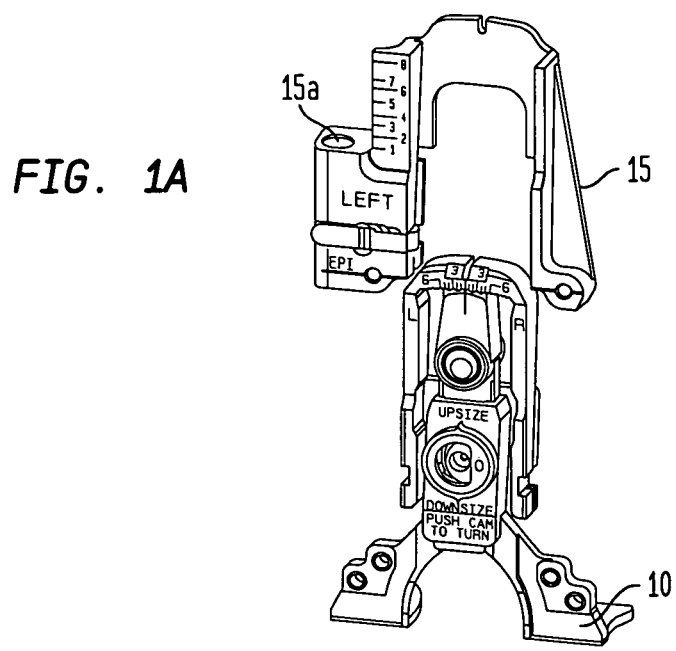
FIGS. 1A-1F provide an overview of how a sizer according to one embodiment of the invention can be assembled and attached to a distal portion of a femur.

Referring to FIG. 1A, there is shown a sizer body 10 and sizer module 15. The module is shown in position to be slidably mounted on the body. The module includes a through-hole 15a for mounting one or more types of styli to the module.

Figure 1B:
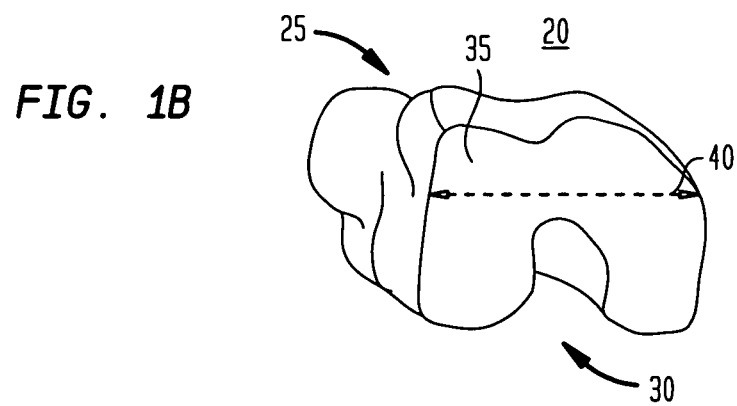

FIG. 1B shows a perspective view of a distal femur portion 20. A generally anterior facing portion of the femur is indicated by reference numeral 25, and a generally posterior facing portion of the femur is indicated by reference numeral 30. The femur has been distally resected, and distal resection plane 35 is a product of such resection. The femur's epicondylar axis is indicated by dotted line 40.

Figure 1C:
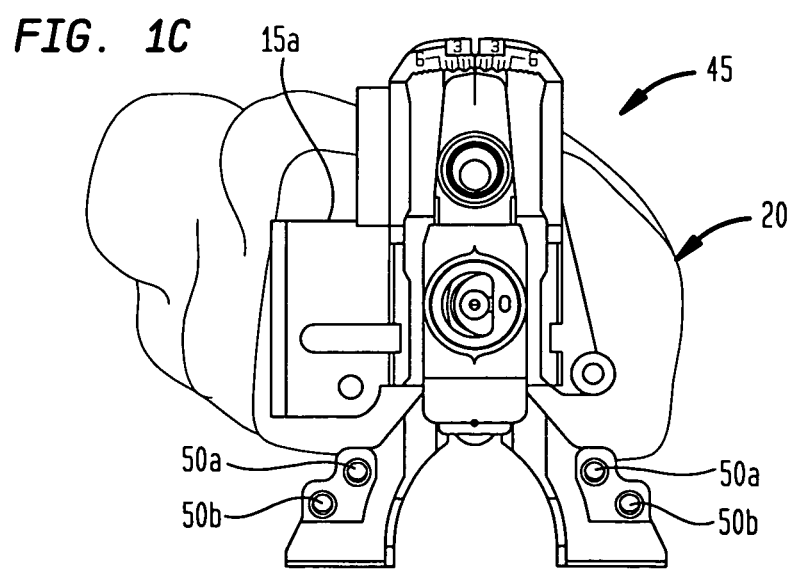

FIG. 1C shows how the body and module of FIG. 1A form an assembly 45 that can then be attached to the distal femur portion of FIG. 1B. The assembly is attached to the distal portion by way of pinholes 50a and/or 50b, through which pins (not shown) are passed to secure the assembly to the femur. Preferably, only one set of holes, either 50a or 50b is used to secure the assembly, the choice being made according to the size of the femur to which the assembly is attached.

Figure 1D:
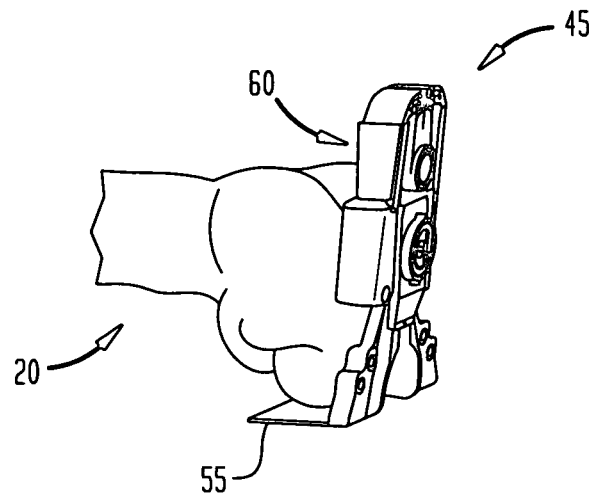

FIG. 1D is an alternate view, from the medial side, of the assembly and distal portion of FIG. 1C. As can be seen from FIG. 1D, the assembly includes a base portion 55 that contacts a posterior portion of the distal femur and a proximal face 60 that contacts the distal resection plane.

Figure 1E:
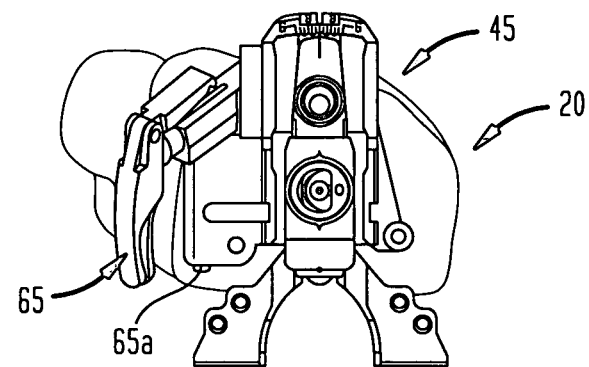

FIG. 1E shows how a mechanical stylus 65 is used with the assembly of FIGS. 1C and 1D. The mechanical stylus together with the body-module assembly makes up a complete AP sizer according to one embodiment of the invention. As can be seen from FIG. 1E, the mechanical stylus is coupled to the assembly via a coupling rod 65a that is secured within through-hole 15a. The rod is free to turn within the through-hole so that the stylus can be rotated about the rod's longitudinal axis, and is free to move in a longitudinal direction within through-hole 15a so that the stylus can moved in a direction parallel to the longitudinal axis of hole 15a.

Figure 1F:
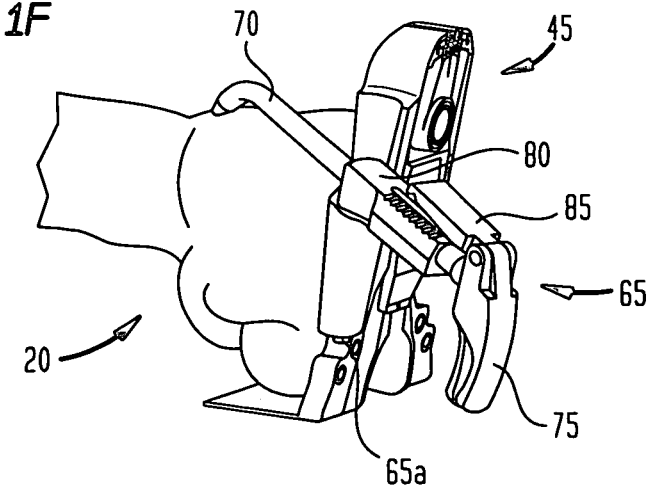

FIG. 1F is an alternate view, from the medial side, of the sizer and distal portion of FIG. 1E. As can be seen in FIG. 1F, the stylus includes an arm 70 that is used for locating points on the anterior cortex of the femur. The stylus also includes a handle 75 that is attached to the arm, and a stylus body 80 that is attached to rod 65a and includes a through-hole for accommodating the stylus arm. The handle is used to translate and rotate the arm within the stylus body's through-hole. A latch 85 is provided for locking the arm in a desired translation position and rotational orientation.

Having provided an overview of one preferred embodiment of the invention, a more detailed description of preferred embodiments will be provided.

Figure 2:
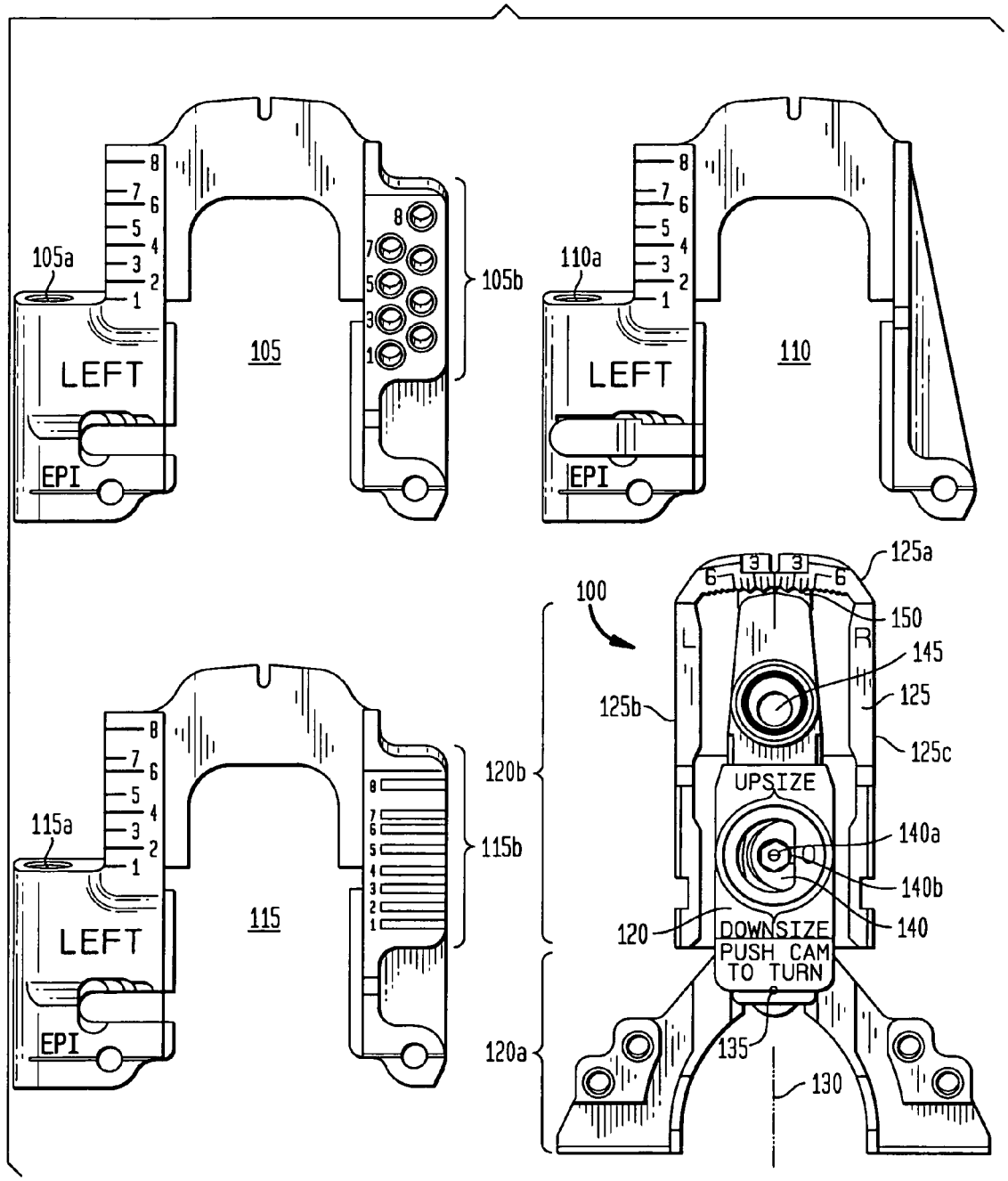
FIG. 2 shows an AP sizer body and three alternative sizer modules that can be removably attached to the body.

Referring to FIG. 2, there is shown an AP sizer body 100 and three alternative sizer modules 105, 110 and 115. Each of the sizer modules can be removably attached to the body. Module 105 is a module that can be used for implant sizing by either a mechanical stylus or navigation stylus inserted in through-hole 105a, or by drill sizing via drill guide holes 105b. Module 110 can only be used for sizing by a mechanical stylus or navigation stylus inserted in through-hole 110a. Module 115 is a module that can be used for implant sizing by either a mechanical stylus or navigation stylus inserted in through-hole 115a, or by blade runner sizing via blade slots 115b.

The body 100 of FIG. 2 is made up a central part 120 and an outer part 125. The central part includes a base 120a and a trunk 120b. The outer part includes a top 125a and sides 125b and 125c. For purposes of this description, the portions of the central and outer parts that face away from the distal portion of the femur when the body is attached to the femur will be referred to respectively as the "central part distal face" and "outer part distal face;" and the portions of central and outer parts that face toward the distal portion of the femur when the body is attached to the femur will be referred to respectively as the "central part proximal face" and "outer part proximal face."

In any event, the outer part of the body and the central part of the body can be moved relative to one another. More specifically, the outer part can be both translated relative to the central part and rotated relative to the central part. The outer part can be translated relative to the central part in a direction parallel to the central part's longitudinal axis (as depicted by line 130). The outer part can be rotated relative to the central part about an axis perpendicular to the central part distal face, such as an axis perpendicular to the central part distal face and passing through point 135.

Movement of the outer part of the body relative to the central part of the body is controlled by two independently operated mechanisms. Translational movement of the outer part relative to the central part is controlled by a rotating element 140, and rotational movement of the outer part relative to the central part is controlled by a push-button 145.

To translate the outer part of the body relative to the central part, one inserts a suitably shaped instrument into a matching recess 140*a* in the rotation element, presses the element down toward the central part proximal face to unlock the element, and then rotates the instrument to rotate the element. A mechanical link causes the outer part to translate relative to the inner part when the element is rotated. Preferably, the translational movement is infinitely variable within a predetermined range. Further, the rotating element preferably includes a detent 140*b* that mates with a protrusion on the central part of the body when the translation position is in the middle of the predetermined range, such that a positive confirmation of the middle position is provided.

To rotate the outer part of the body relative to the central part, one presses push-button 145 down toward the central part proximal face. The button is linked to a restraining element 150 having a multiple of teeth that mesh with teeth on the top of the outer part. When the button is pushed, the restraining element moves away from the top of the outer part (i.e. in a direction toward the base of the central part), and thereby the teeth of the restraining element are decoupled from the teeth on the top of the outer part. Once the restraining element and outer part are decoupled, the outer part is free to rotate about axis 135. After the outer part has been rotated to the desired position, the button is allowed to return to its original position, causing the restraining element to once again mesh with the top of the outer part and thereby locking the outer part in the desired position. The meshed teeth arrangement of the restraining element and the top of the outer part preferably provide rotation in 1 degree increments. However, it should be noted that the teeth can be arranged such that the increments are other than 1 degree. Moreover, the teeth can be eliminated so as to provide an infinitely variable adjustment.

Figure 3:
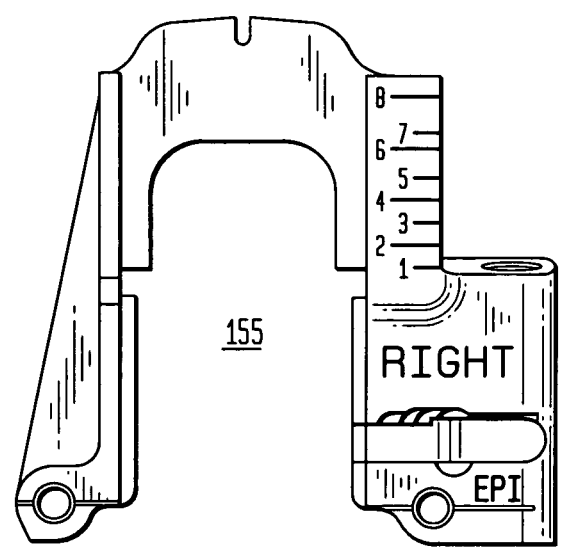
FIG. 3 shows yet another alternative AP sizer module that can be removably attached to the body of FIG. 2.

Each of the modules depicted in FIG. 2 are designed for use in left-knee arthroplasty. However, all of the embodiments detailed in this description are equally applicable in the context right-knee arthroplasty. In view of this description one skilled in the art of knee arthroplasty will readily appreciate how the embodiments detailed in this description apply in right-knee arthroplasty. For purposes of providing an example of how a right-knee embodiment is implemented, FIG. 3 is provided. FIG. 3 shows a module 155 that is the right-knee analogue of module 110.

Figure 4:
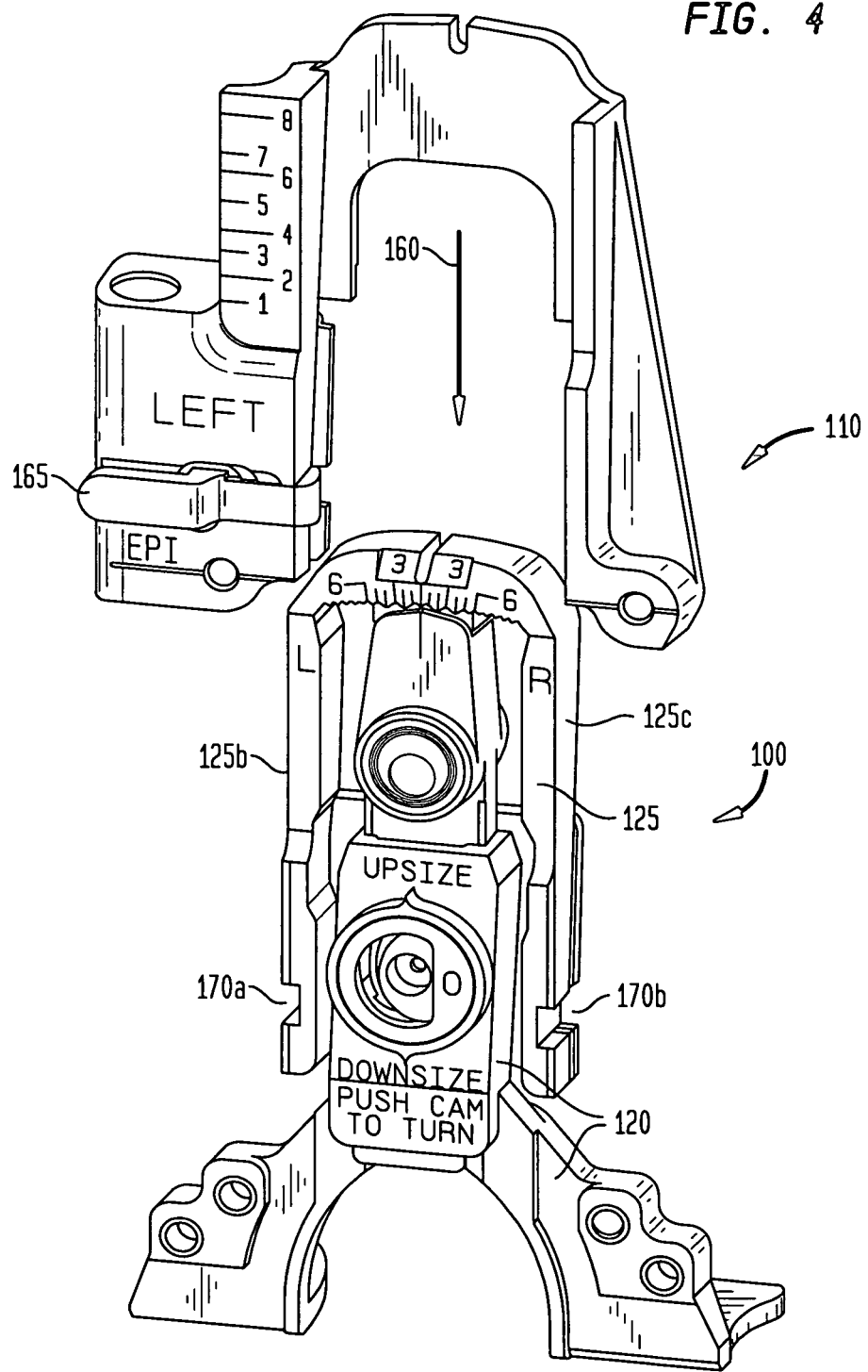
FIG. 4 is a perspective view of how module 110 of FIG. 2 is removably attached to the body of FIG. 2.

In any case, each of the modules depicted in FIGS. 2 and 3 may be removably attached to the outer part of the body. To illustrate how such attachment is achieved, FIG. 4 is provided. FIG. 4 is a perspective view of how module 110 of FIG. 2 is removably attached to body 100 of FIG. 2. As can be seen from FIG. 4, the module is positioned over the top of outer part 125 and is moved downward onto the outer part, as indicated by arrow 160. In a preferred embodiment, sides 125*b* and 125*c* of the outer part include grooves for guiding the module as it slides into its attached position. A latch 165 on the module mates with a catch 170*a* on the body to lock the module in place when the module reaches its attached position. A second catch 170*b* is provided for locking a module having a latch on the opposite side of the outer part, such as module 155 of FIG. 3.

Figure 5:
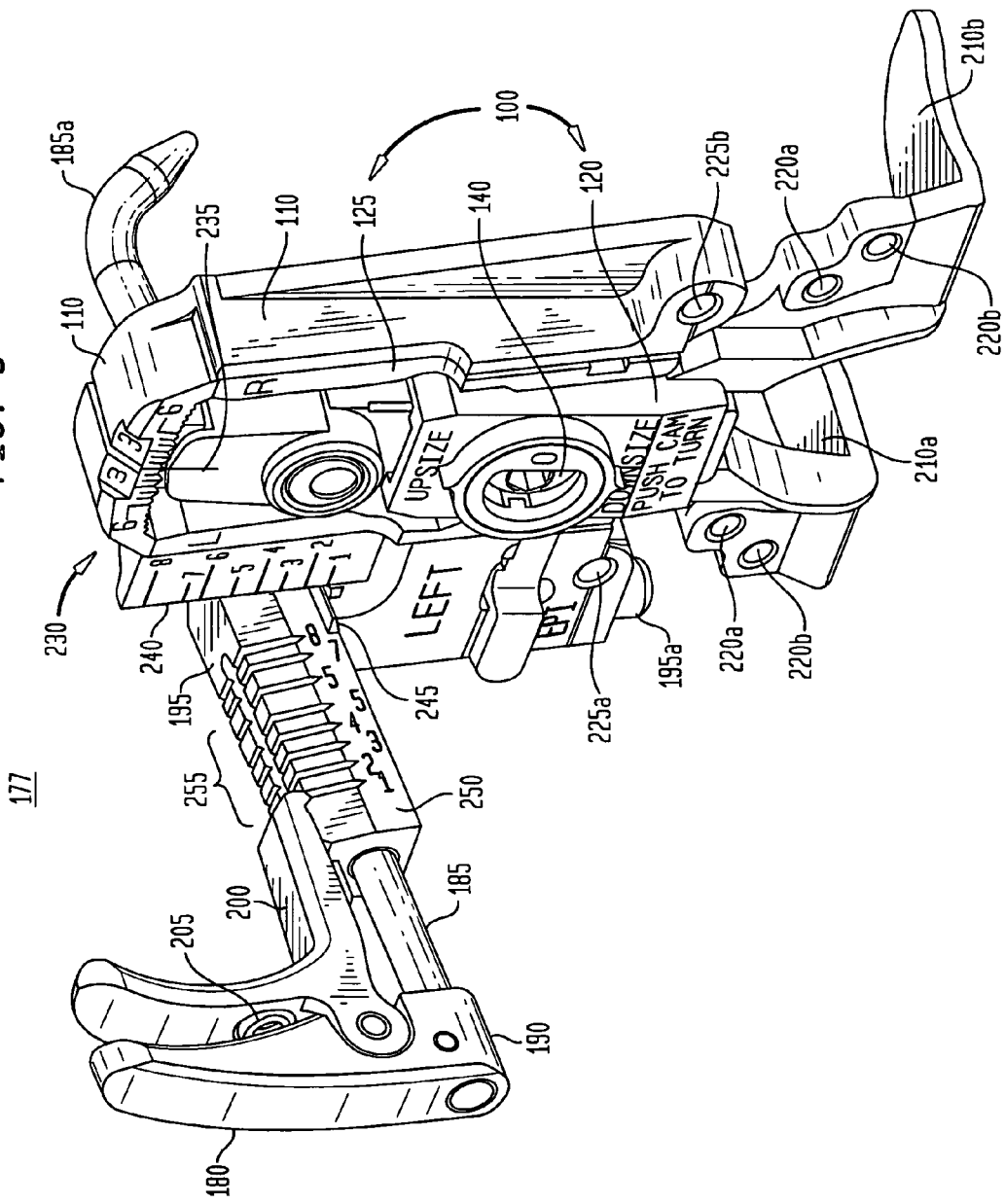
FIG. 5 is a perspective view of an assembled sizer including a mechanical stylus in addition to the body 100 and module 110 of FIG. 4.
Figure 6:
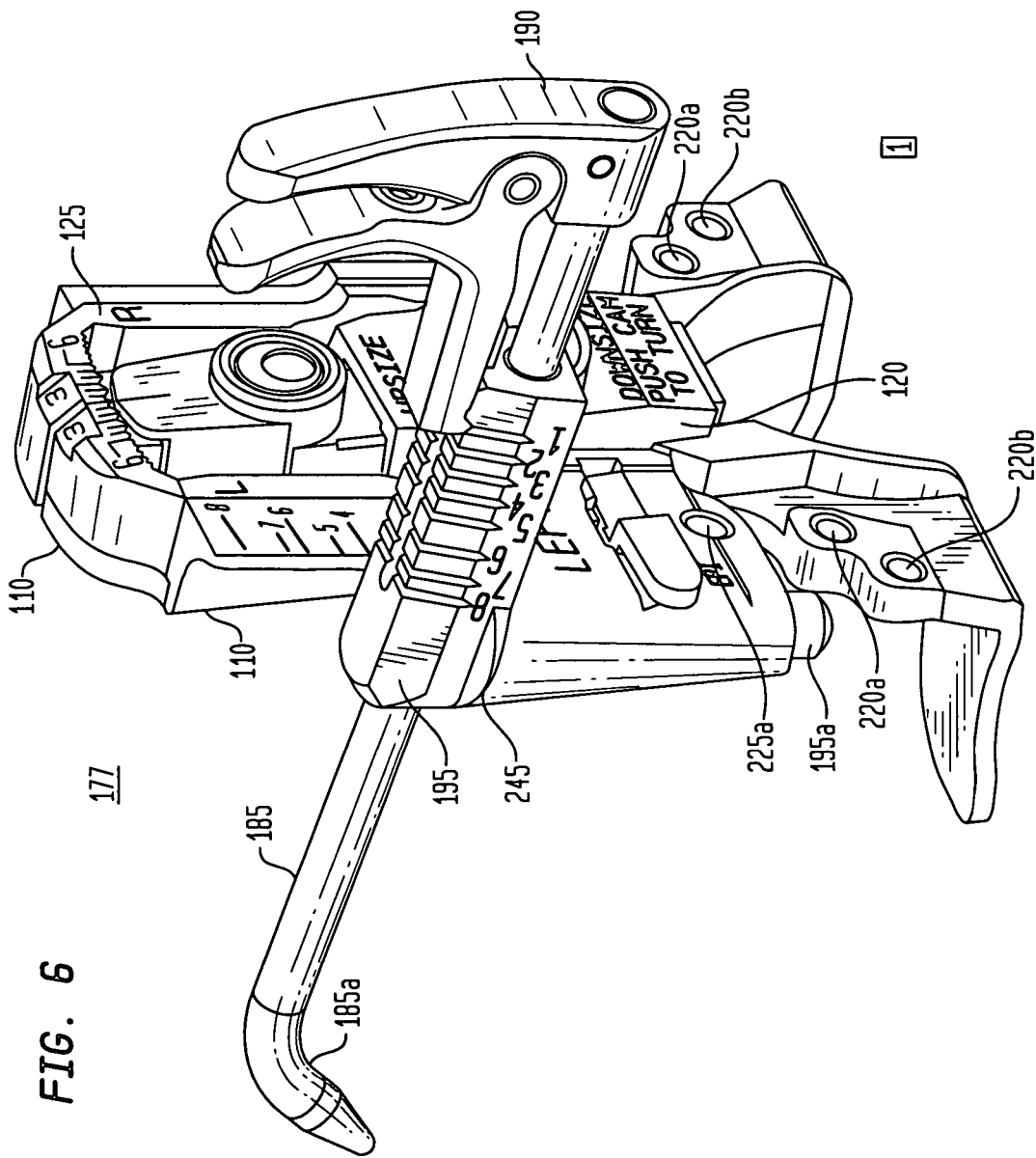
FIG. 6 is an alternative perspective view of the sizer of FIG. 5.

FIG. 5 is a perspective view of an assembled sizer 177 including a mechanical stylus 180 in addition to the body 100 and module 110 of FIG. 4. FIG. 6 is an alternative perspective view of the sizer of FIG. 5.

Referring now to FIGS. 5 and 6, the stylus includes an arm 185 with a curved tip 185*a* that is used for locating points on the anterior cortex of the femur. The stylus also includes a handle 190 that is attached to the arm and a stylus body 195 that is attached to a rod 195*a*. Through-hole 110*a* (see FIG. 2) accommodates the rod such that the stylus is free to rotate about the longitudinal axis of the rod and is free to translate longitudinally such that the stylus may move in a direction along the hole's longitudinal axis. The handle can be used to translate the arm within the stylus body's through-hole in a direction parallel to the stylus body's longitudinal axis. The handle is also used to rotate the arm about the arm's longitudinal axis. A latch 200 is provided for locking the arm in a desired translation position and in the rotation position in which the handle is in a generally aligned with the longitudinal axis of rod 195*a*. The latch is spring loaded with respect to the handle by a spring 205. To release the latch, finger pressure is applied to the latch so as to compress the spring.

The sizer depicted in FIG. 5 is similar to the sizer depicted in FIGS. 1E and 1F. Accordingly, reference to FIGS. 1E and 1F is helpful in understanding how the sizer of FIG. 5 is employed to size a femur.

Notably, the orientation of handle 180 of the FIG. 5 sizer is rotated 180 degrees relative to the orientation of handle 75 of the FIG. 1E/1F sizer. Orienting the handle as shown in FIG. 5 facilitates manipulation of the stylus during knee arthroplasty by positioning the handle away from the incision area.

The sizer of FIG. 5 is used to determine correct implant size and cutting block pin position by referencing the posterior condyles of the distal femur. More specifically, the sizer is aligned with the posterior condylar axis through two skids 210*a* and 210*b* located on the base of the sizer body. The skids are positioned to contact the posterior condyles while the body is centered, or approximately centered, on the femur with respect to the medial-lateral direction. An example of such positioning is seen in FIGS. 1E and 1F.

Once the body is properly positioned, pins can be passed through either pair of pinholes 220*a* or 220*b*, or through both pairs of pinholes 220*a* and 220*b*, to secure the body to the femur. In a preferred embodiment, the body 100, module 110, and stylus 180 are removably attached to each other to form a complete assembly, and then the complete assembly is attached to the femur via the pinholes.

In another preferred embodiment, the body of the sizer is first attached to the distal resection plane and the appropriate module is mounted on the body after the body has been attached. Accordingly, it is not necessary that a module be attached to the body during attachment of the body to the femur.

In still another preferred embodiment, the body is first attached to the femur, and the module and stylus are then attached to each other prior to attaching the module and stylus to the body.

In yet another preferred embodiment, the stylus is not removably attached to the module. Rather, the stylus and module are fixed to each other such that they form a permanent sub-assembly. In such an embodiment, the preferred method of use is to attach the body to the femur apart from the module/stylus sub-assembly, and then removably attach the module/stylus sub-assembly to the body.

In any event, once the complete sizer is correctly positioned on the femur, the internal-external rotation of the implant is set by setting the internal-external rotation of the sizer. In this regard, it is important to note that the sizer module includes two drill guide holes 225a and 225b, which relate to a cutting block type which, in turn relates to a type of implant. Upon final setting of the sizer, holes are drilled in the femur at positions determined by the guide holes. Thus, the sizer setting determines the guide hole positions, which determines the cutting block position which, in turn, determines the implant position. Therefore, by setting the internal-external rotation of the sizer, the internal-external rotation of the implant is being set.

To set the internal-external rotation of the sizer, the outer part of the sizer body is rotated relative to the central part of the sizer body. Since the central part of the sizer body is fixed relative to the posterior condylar axis, and both the central and outer parts of the sizer body are fixed relative to the distal resection plane, the rotation of the outer part of the body relative to the center part has the effect of changing the inclination between the posterior condylar axis as projected onto the distal resection plane and an imaginary line connecting the drill guide holes as projected onto the distal resection plane. The change in magnitude of such inclination is equal to the internal-external rotation.

The outer part of the body is rotated by depressing push-button 145, moving the outer part to the desired position, and then releasing the push button to lock the outer part in place. The degree of internal-external rotation is read from a scale 230 located at the top of the outer part. The scale is referenced to a mark 235 on the central part of the sizer body.

After the internal-external rotation of the implant is set, the stylus can be used to size the femur. That is, the stylus can be used to determine the appropriate size implant needed for the subject femur. To size the femur, a practitioner manipulates the stylus handle such that the curved tip 185a of the stylus contacts the anterior cortex of the femur at the point where the anterior-superior point of the implant should contact the anterior cortex of the femur (the "desired run-out point"). Once the tip is contacting the desired run-out point, the practitioner reads the size from an anterior-posterior sizing scale ("AP scale") 240 located on the distal face of the module. The reading is taken by comparing a lip 245 on the stylus body to the AP scale. For example, if the lip is pointed toward the number "3" of the AP scale, then the femur size is a "3" and the implant needed is a size "3."

A further indication of implant size is provided by a superior-inferior run-out scale ("SI scale") 250. The SI scale is associated with a multiple of notches 255 that are etched into the stylus body, each notch being associated with a corresponding size. When the curved tip of the stylus has been located at the desired run-out point, the latch is allowed to settle into the notch that most closely corresponds to the stylus position. The number associated with the notch into which the latch settles is the femur/implant size as measured by the SI scale. For example, if the latch sits in the notch corresponding to the number "3" of the SI scale, then the SI scale indicates a femur/implant size of "3."

If the size as measured by the SI scale does not match the size as measured by the AP scale, it is an indication that the anterior portion of the implant will not run-out of the femur at the desired run-out point. In other words, it is an indication that the anterior portion of the implant will not mate with the anterior portion of the resected femur at the ideal position. In common terminology, a mismatch in size measurements is an indication that the implant may "notch" or "overhang".

The sizer provides a mechanism for adjusting position of the implant to avoid "notching" and "overhanging." More particularly, when the size as measured by the SI scale does not match the size as measured by the AP scale, the practitioner positions the stylus such that the latch settles into a notch 255 corresponding to size as measured by the AP scale. In this condition, with the stylus positioned such that the lip is at the measured AP size and the curved tip is over the desired run-out point, the practitioner can observe the degree to which the implant will "notch" or "overhang." If the curved tip lies above the desired run-out point when the AP and SI scales read the same size, the distance between the tip and the desired run-out point indicates the "overhang" magnitude. If, the stylus can not be moved far enough down the AP scale due to premature contact of the femur and curved tip, the distance between the point on the scale where the stylus stops and the point corresponding to the measured AP size indicates the "notch" magnitude.

It should be noted that it is the sizer geometry that makes run-out estimations possible. More particularly, the sizer is configured such that the plane within which the stylus arm 185 moves when the stylus is rotated about the longitudinal axis of rod 195a is parallel to the plane of the anterior resection. Thus, translation of the stylus arm along its longitudinal axis reflects translation of the plane of the anterior resection.

The plane within which the stylus arm moves when the stylus is rotated about the longitudinal axis of rod 195a is determined by the inclination of through-hole 110a relative to the distal resection plane. When the stylus is positioned in the through-hole, the longitudinal axis of rod 195a is oriented at the same inclination as the through-hole. In this manner, the angle formed between the longitudinal axis of rod 195a and the distal resection plane determines the plane in which the stylus arm moves when rotated about the longitudinal axis of the rod. Accordingly, the inclination of through-hole 110a relative to the distal resection plane is set such that the plane within which the stylus arm moves is parallel to the plane of the anterior resection.

In any event, when a "notch" or "overhang" is indicated, a correction can be made by shifting the implant. That is, for a given size implant, the implant can be shifted such that it properly mates with the desired run-out point. This is done using rotating element 140 to translate the outer part of the sizer body relative to the central part. For example, in an "overhanging" situation the rotating element is used to move the outer part in a generally posterior direction which, in turn, moves the module in the generally posterior direction, and thus moves the drill guide holes 225a and 225b in the generally posterior direction. Since the hole position corresponds to the cutting block and implant position, movement of the drill guide holes in a generally posterior direction results in corresponding movement of the implant in the generally posterior direction. In this manner, the run-out point for a given size implant can be adjusted to correct for an "overhanging" situation.

In a similar manner, a shift of implant position can be made to correct a "notching" situation. To correct for a "notching"

situation, the rotating element is used to move the outer part in a generally anterior direction which, in turn, moves the implant in the generally anterior direction.

The sizer of FIGS. 5 and 6 offers several advantages when used during minimally invasive surgery (MIS). One advantage is that the stylus 180, through-hole 110*a*, and AP scale 240 are positioned on the same side of the sizer so that the bulk at the other side of the sizer is minimized. Another advantage is that the stylus can rotate about the longitudinal axis of the stylus arm. Such rotation allows the curved tip 185*a* to be rotated for easy insertion under the soft tissue, and then rotated back into position to contact the desired run-out point. Thus, the stylus arm can be more easily maneuvered about the soft tissue, and therefore disturbance of the soft tissue is minimized.

Figure 7:
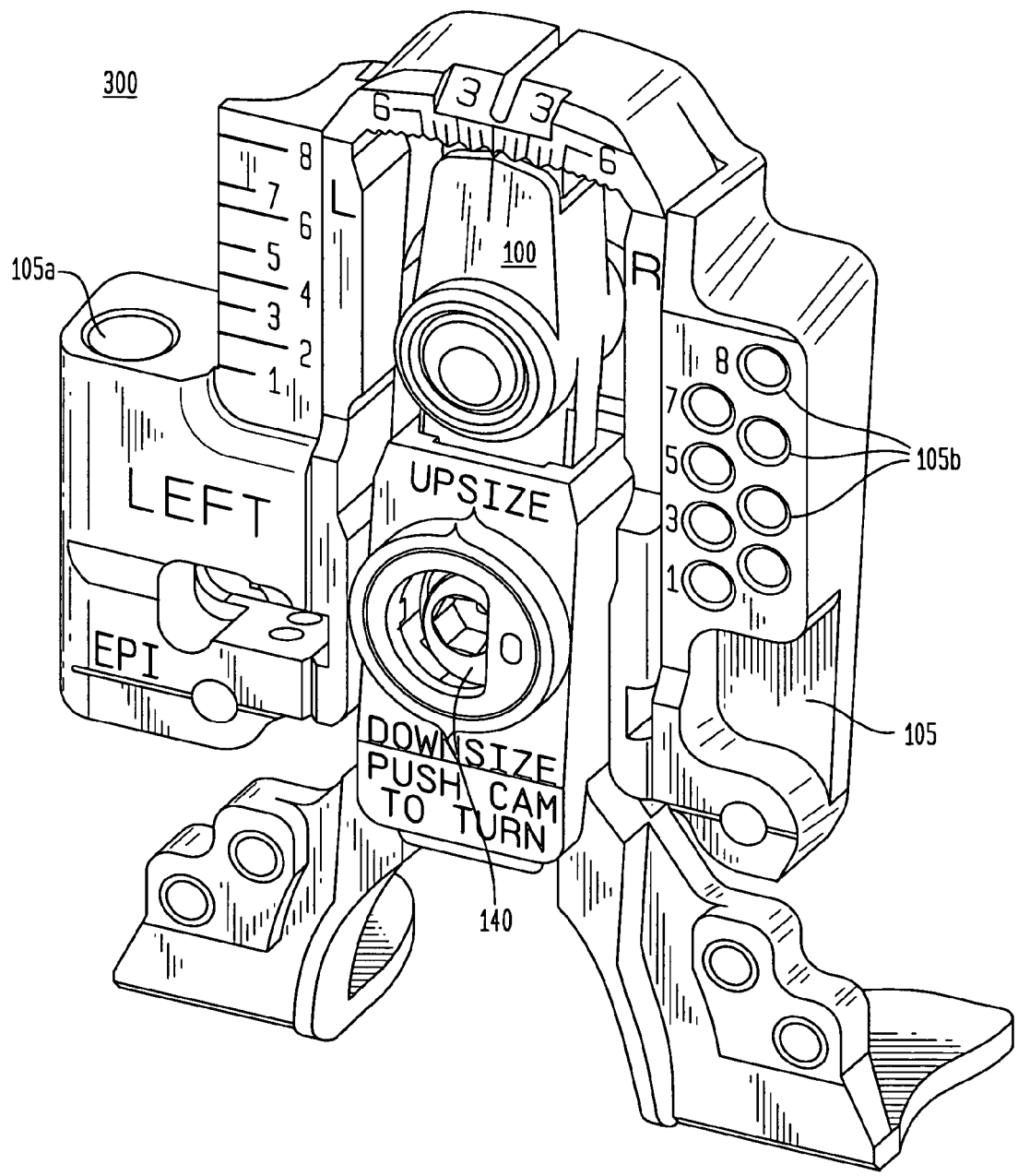
FIG. 7 is a perspective view of an assembly including body 100 and module 105 of FIG. 2.

Turning now to FIG. 7, there is shown a perspective view of an assembly including body 100 and module 105 of FIG. 2. The assembly is an AP sizer 300 in accordance with an embodiment of the invention. The sizer 300 can be used to implement sizing through a mechanical stylus or through drill sizing.

Sizer 300 is the same as sizer 177 of FIGS. 5 and 6 with one exception, the module of FIG. 7 includes the multiple drill guide holes 105*b*. Each hole is associated with a femur/implant size, and to this end the drill guide holes are marked with sizes to clearly indicate the relationship between each hole and its respective size. For example, as seen in FIG. 7, there are eight drill guide holes and markings "1," "3," "5," "7" and "8" are included on the module so that the association between holes and femur/implant sizes is clear. The holes corresponding to sizes "2," "4" and "6" are clear from the markings for holes "1," "3," "5," "7" and "8." The sizes 1-8 may be the sizes associated, for example, with the Triathlon® line of implants.

When sizer 300 is used for drill sizing, the procedures of attaching the sizer body to the femur, attaching the module to the body, and setting the I/E rotation are the same as for sizer 177. However, once the sizer is attached to the femur and rotation has been set size is measured by drilling holes in the femur rather than through use of a stylus. More specifically, holes are drilled in the femur while using drill guide holes 105*b* to guide the drill bit. In this manner, the drill bit enters the femur through the distal resection plane. The bit may or may not exit the femur at the anterior cortex.

The longitudinal axes of the drill guide holes 105*b* are inclined relative to a plane perpendicular to the distal resection plane such that the inclination of the holes matches the inclination of the anterior resection. Thus, when the drill bit passes into the bone, it follows a path that corresponds to the anterior resection. Therefore, the point where the drill bit exits the anterior cortex—or would exit the anterior cortex if it were long enough—is the point where the anterior resection will meet the anterior cortex of the femur. Ideally, the point of exit is the desired run-out point. To this end, the practitioner picks a drill guide hole that is likely to result in an exit point anterior to the desired run-out point and drills a hole using the selected guide. The practitioner observes the exit point and determines whether a better result can be achieved by selecting a different guide hole and drilling again, at all times being careful not to choose a hole that will result in an exit point posterior to the desired run-out point. If the practitioner believes a better result can be achieved by using a different guide hole, the practitioner drills again using the different guide hole to guide the drill bit. When the practitioner believes that further drilling can not achieve an exit point any closer to the desired run-out point than the last exit point, drill sizing is complete. The determined size of the femur/implant is read from the corresponding drill guide hole. The determined size is the size associated with the guide hole that was used to drill the best hole.

As in the embodiment of FIGS. 5 and 6, in the embodiment of FIG. 7, the rotating element 140 can be used to shift the implant so as to correct for a "notching" or "overhanging" situation. Thus, if the exit point of the best drilled hole is posterior to the desired run-out point the rotating element can be used to move the outer part of the sizer body in a generally anterior direction which, in turn, moves the implant in the generally anterior direction. If the exit point of the best drilled hole is anterior to the desired run-out point the rotating element can be used to move the outer part of the sizer body in a generally posterior direction which, in turn, moves the implant in the generally posterior direction.

When the sizer of FIG. 7 is used for sizing with a mechanical stylus, sizing is performed in the same manner as discussed in connection with FIGS. 5 and 6, with the stylus being removably attached to module 105 via through-hole 105*a*.

Figure 8:
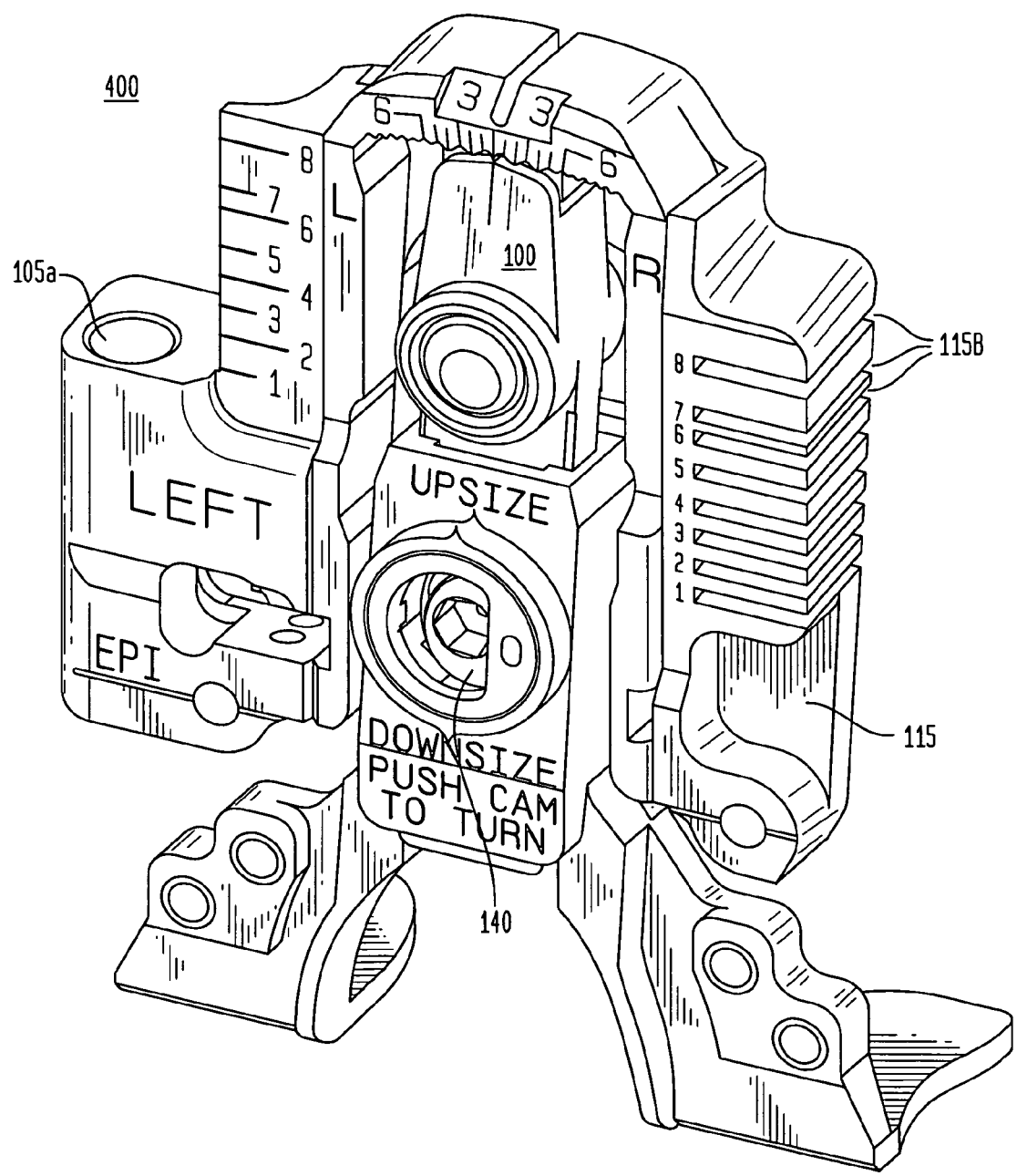
FIG. 8 is a perspective view of an assembly including body 100 and module 115 of FIG. 2.

FIG. 8 is a perspective view of an assembly including body 100 and module 115 of FIG. 2. The assembly is an AP sizer 400 in accordance with an embodiment of the invention. The sizer 400 can be used to implement sizing through a mechanical stylus or through blade runner sizing. Sizer 400 is the same as sizer 300 of FIG. 7 with one exception, the module of FIG. 8 includes multiple blade slots 115*b*. Each slot is associated with a femur/implant size, and to this end the slots are marked with sizes to clearly indicate the relationship between each slot and its respective size. For example, as seen in FIG. 8, there are eight slots and markings "1" through "8" are included on the module so that the association between the slots and femur/implant sizes is clear. The sizes "1-8" may be the sizes associated, for example, with the Triathlon® line of implants.

When sizer 400 is used for blade runner sizing, the procedures of attaching the sizer body to the femur, attaching the module to the body, and setting the I/E rotation are the same as for sizers 177 and 300. However, once the sizer is attached to the femur and the rotation has been set, size is measured by inserting a blade into one of the blade slots rather than through use of a stylus. More specifically, the practitioner places the blade in a slot that he believes to be co-planar with the correct plane for the anterior resection.

The planes of the slots are parallel to each other and are inclined relative to a plane perpendicular to the distal resection plane such that the inclination of the slots matches the inclination of the anterior resection. Thus, when the blade is sitting in a slot, it lies along a path that corresponds to the anterior resection. Therefore, by observing the plane of the blade one can visualize where the plane of the blade intersects the anterior cortex of the femur. Accordingly, the practitioner picks a slot that he believes will result in a resection plane that intersects the anterior cortex as the desired run-out point and inserts the sizing blade. The practitioner observes the intersection of the blade plane and the anterior cortex and adjusts the slot selection according to the result. When the practitioner believes that the blade is in the slot that corresponds to an intersection point closest to the desired run-out point and that no other slot can provide a better intersection point, blade runner sizing is complete. The determined size of the femur/implant is read from the slot's associated numeral. The size of the femur/implant is the size associated with the slot that provides the best intersection point.

As in the embodiments of FIGS. 5, 6 and 7, in the embodiment of FIG. 8 the rotating element 140 can be used to shift the implant so as to correct for a "notching" or "overhanging" situation. Thus, if the slot chosen in blade runner sizing indicates an intersection point anterior to the desired run-out point the rotating element can be used to move the outer part of the sizer body in a generally posterior direction which, in turn, moves the implant in the generally posterior direction. If the slot chosen during blade runner sizing indicates an intersection point posterior to the desired run-out point the rotating element can be used to move the outer part of the sizer body in a generally anterior direction which, in turn, moves the implant in the generally anterior direction.

When the sizer of FIG. 8 is used for sizing with a mechanical stylus, sizing is performed in the same manner as discussed in connection with FIGS. 5, 6 and 7 with the stylus being removably attached to module 115 via through-hole 115*a*.

Figure 9:
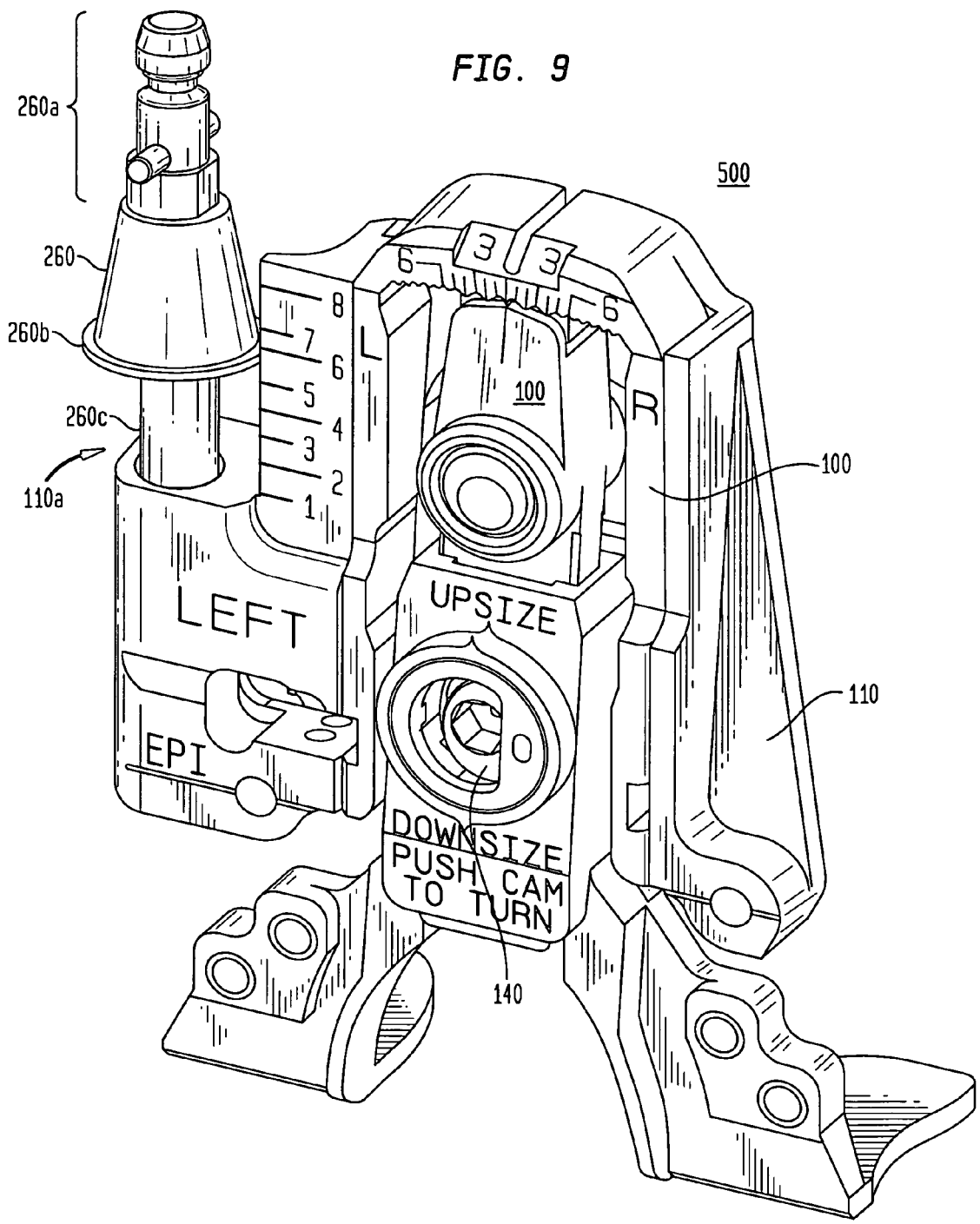
FIG. 9 is a perspective view of a sizer including body 100 of FIG. 2, module 110 of FIG. 2. and a navigation stylus.

FIG. 9 is a perspective view of a sizer including body 100 of FIG. 2, module 110 of FIG. 2, and a navigation stylus 260. The navigation stylus includes a head 260*a* to which a navigation tracker can be attached, a lip 260*b* which is used with scale 240 to obtain size readings, and a shaft 260*c* which is accommodated within though-hole 110*a*. The longitudinal axis of the shaft is perpendicular to the plane defined by lip 260*b*.

The navigation tracker used with stylus 260 communicates with a navigation camera system. The communications between the tracker and camera system are used by a computer to generate a virtual three-dimensional Cartesian coordinate system (x-axis, y-axis, and z-axis) that is fixed in space relative to the tracker. Any movement of the tracker results in corresponding movement of the three-dimensional coordinate system. Further, the three dimensional coordinate system is established so that one of the planes defining the system (the x-y plane) is parallel to the plane defined by lip 260*b* and so that the coordinate axis perpendicular to such plane is parallel to the longitudinal axis of the stylus shaft. Thus, once the sizer is set to the correct I/E rotation, the x-y plane and lip plane are parallel to the plane of the anterior resection.

When using sizer 500 to size a femur/implant, the procedures of attaching the sizer body to the femur and attaching the module to the body are the same as for sizers 177, 300 and 400. The procedure of setting the I/E rotation may be the same as for sizers 177, 300 and 400, though the I/E rotation may be alternatively set through navigation.

In any event, the practitioner uses a hand-held tracker to map one or more femoral landmarks to the coordinate system associated with the navigation stylus. That is, a second tracker is used to determine the position of one or more femoral landmarks relative to the coordinate system associated with the navigation stylus.

Once the sizer has been attached to the femur and the landmark(s) have been established, the stylus can be translated within through-hole 110*a* to size the femur. As the stylus is translated within through-hole 110*a*, the computer compares the position of the x-y plane to the femoral landmark(s). When the stylus is positioned such that the plane of the anterior resection—as reflected by the x-y plane position—intersects the desired run-out point, the sizing is complete. The size reading is taken by observing the position of lip 260*b* relative to the AP scale. For example, if the lip is pointed toward the number "3" of the AP scale, then the femur/implant size is "3."

As in the embodiments of FIGS. 5, 6, 7 and 8, in the embodiment of FIG. 9 the rotating element 140 can be used to shift the implant so as to correct for a "notching" or "overhanging" situation.

As these and other variations and combinations of the features discussed above can be utilized without departing from the present invention as defined by the claims, the foregoing description of the preferred embodiments should be taken by way of illustration rather than by way of limitation of the invention as defined by the claims.

The invention claimed is:

1. A system for sizing a distal portion of a femur during knee arthroplasty, comprising:
    a body that can be removably attached to the distal portion of the femur, the body includes a top portion, a bottom portion, lateral sides, each lateral side has a catch, and a central longitudinal axis extending through the top portion and bottom portion; and
    at least two modules, each module having a latch to engage one of the catches so that each module is removably attachable to the body such that the body with an attached module is operable for use in measuring a size of the distal portion of the femur,
    the at least two modules including at least one module specific to right-knee arthroplasty and at least one module specific to left-knee arthroplasty,
    wherein each module is configured to support a stylus that is removably attachable to the module, each module supporting the stylus by way of a through-hole that is formed in the module, the through-hole being formed such that when the latch of the module is engaged with one of the catches of the body a central longitudinal axis of the through-hole is not perpendicular to the central longitudinal axis of the body, and when the latch of the module is engaged with one of the catches of the body and the body is attached to the distal portion of the femur the central longitudinal axis of the through-hole is substantially perpendicular to an anterior resection plane of the femur.

2. The system as set forth in claim 1, wherein the body further comprises a plurality of pinholes through which the body may be removably attached to the distal portion of the femur.

3. The system as set forth in claim 1, wherein each module is removably attachable to the body through sliding of the module onto the body.

4. The system as set forth in claim 1, further comprising a mechanical stylus.

5. The apparatus as set forth in claim 1, further comprising a navigation stylus.

6. The apparatus as set forth in claim 1, further comprising a module that is operable for use in performing drill sizing of the distal portion of the femur.

7. The apparatus as set forth in claim 1, further comprising a module that is operable to support blade runner sizing of the distal portion of the femur.

8. The system as set forth in claim 1, wherein the at least two modules include at least one module that is operable to support sizing of the distal portion of the femur according to more than one sizing methodology.

9. A method for sizing a distal portion of a femur during knee arthroplasty, comprising the steps of:
    providing the system according to claim 1,
    removably attaching a module from the at least two modules to the body;
    removably attaching the module from the at least two modules and the body to the distal portion of the femur; and
    using the module from the at least two modules and the body to size the distal portion of the femur according to a methodology.

10. The method as set forth in claim 9, further comprising the steps of:
    removing the module from the at least two modules from the body;

removably attaching another module to the body from the at least two modules; and using the other module from the at least two modules and the body to size the distal portion of the femur according to another methodology.

* * * * *